United States Patent [19]
Lloyd

[11] Patent Number: 5,301,633
[45] Date of Patent: Apr. 12, 1994

[54] FLEXIBLE BLADDER FOR SOAKING THE EARTH AND COLLECTING EARTHWORMS AND METHOD OF USE

[76] Inventor: Thomas G. Lloyd, 264 E. Wymoning St., St. Paul, Minn. 55107

[21] Appl. No.: 94,498

[22] Filed: Jul. 19, 1993

[51] Int. Cl.⁵ .............................................. A01K 67/00
[52] U.S. Cl. ..................... 119/6.7; 239/145; 47/79
[58] Field of Search .............. 119/6.7; 239/55, 34, 239/145; 47/79, 80, 27, 48.5

[56] References Cited

U.S. PATENT DOCUMENTS

| | | |
|---|---|---|
| 1,446,914 | 2/1923 | Lebiedzinki et al. |
| 2,754,624 | 7/1956 | Wester ............................. 47/79 |
| 2,814,529 | 11/1957 | Arnt . |
| 2,867,055 | 1/1959 | Lebiedzinski . |
| 3,195,818 | 7/1965 | Herberg .......................... 239/145 |
| 3,239,413 | 3/1966 | Chaney . |
| 3,900,135 | 8/1975 | Stephens ........................ 47/48.5 |
| 4,001,968 | 1/1977 | Green . |
| 4,130,245 | 12/1978 | Bryson ............................ 239/34 |
| 4,219,600 | 8/1980 | Surowitz et al. . |
| 4,231,188 | 11/1980 | McGuire et al. . |
| 4,245,434 | 1/1981 | Green . |
| 4,887,386 | 12/1989 | Minshull ........................... 47/79 |
| 5,020,271 | 6/1991 | Walker . |
| 5,067,272 | 11/1991 | Constantz . |

FOREIGN PATENT DOCUMENTS

2019423 2/1972 Fed. Rep. of Germany .......... 47/80

*Primary Examiner*—Gene Mancene
*Assistant Examiner*—Todd E. Manahan
*Attorney, Agent, or Firm*—Robert C. Baker

[57] ABSTRACT

A flat and thin bladder device is used to cause earthworms to migrate to the earth's surface for easy collection. The bladder is laid flat on the earth's surface and has a maximum thickness between its top wall and bottom wall of not over about 5 centimeters but has area dimensions greater than 1 meter in all directions and not greater than about 4 meters in all directions. The maximum thickness of the bladder is limited by a pattern of spaced connections between the top wall and bottom wall forming the bladder. At least the bottom wall is opaque to block out light under it, and the bottom wall has a plurality of openings that are substantially uniformly distributed for the escape of water from the bladder to earth underlying the bottom wall. Water is introduced to the bladder at a rate about equal to the rate of water escaping from the bottom wall. Soaking the earth under the bladder causes earthworms to migrate to the surface and they are then easily collected as portions of the bladder are lifted to expose them.

9 Claims, 1 Drawing Sheet

FLEXIBLE BLADDER FOR SOAKING THE EARTH AND COLLECTING EARTHWORMS AND METHOD OF USE

BACKGROUND OF THE INVENTION

This invention relates to a new device and a new method for collecting earthworms, with due attention to safety for the person collecting the earthworms as well as to safety and freedom from harm or injury to the earthworms being collected.

Collecting earthworms for use as bait in fishing, and particularly the collection of earthworms of night crawler size for that purpose, has been an activity not always accomplished under agreeable conditions. For example, nighttime collection after a rain is commonly recognized as one of the best times to collect earthworms, but the darkness and wetness are not conditions of choice for human comfort. Another problem with nighttime collection is that it is conducted under conditions that seem to be highly favorable to the earthworms, particularly the night crawlers. During nighttime hours they seem to have a sharpened sense for detecting an approaching collector (whether from sound or vibration caused by a collector's movement or from the light of a collector's flashlight, etc.). In any event, night crawlers generally are well on their way striving to get back into the earth by the time a collector reaches out to grab them during nighttime collection efforts.

Digging and turnover of earth has been another way to collect the earthworms needed for fishing, but this approach requires physical effort not always giving commensurate results.

Still further, an electrical device to assist collection has been used, but according to the following newspaper article from the "Saint Paul Pioneer Press" of Saint Paul, Minn. (Jun. 2, 1993 at page 4A), much danger is associated with its use:

"Worm Getter," an electrical probe that is suppose [sic] to shock earthworms into crawling to the surface of the ground where they can be collected for fish bait, is being recalled by retailers because such devices have been putting fishermen underground instead. The Consumer Product Safety Commission said the 83,000 owners of the devices should return them for refunds, following reports that 30 worm hunters have been electrocuted.

Other techniques for collecting earthworms have involved the use of chemicals, but this can be harmful to the earthworms as pointed out in U.S. Pat. No. 1,446,914 as well as in U.S. Pat. No. 3,239,413, both of which teach chemical solutions designed to drive earthworms out of the earth.

Thus, to the extent known, the art has not heretofore had a completely safe and harmless and almost effortless technique for stimulating earthworms to migrate to the earth's surface for easy collection at any time that the person collecting the worms elects to engage in collection. This invention constitutes a breakthrough solution to that problem.

SUMMARY OF THE INVENTION

The invention provides a simple, inexpensive device that may be used during daylight for collecting earthworms. No electricity is required No harsh chemicals are required. Only those conditions to which earthworms have become accustomed are used, and those conditions are artificially created in the practice of the invention.

The new device of the invention is designed to cause earthworms to migrate to the earth's surface for easy collection at any time elected by the collector.

This new device comprises a flexible, substantially flat and thin bladder capable of being laid in flat condition on the earth's surface. The device has a top wall and a bottom wall of flexible sheet material defining the top and bottom limits of the bladder interior, and the bladder has a maximum thickness between the top wall and bottom wall of not over about 5 centimeters when the bladder is filled with water after being laid in flat condition on the surface of the earth. Further, the bladder has area dimensions greater than about 1 meter in all directions transverse to its thickness and not greater than about 4 meters in all directions transverse to its thickness. The maximum thickness of the bladder is limited by the fact that the top wall and the bottom wall are held against greater spacing from each other than about 5 centimeters by a pattern of spaced connections therebetween. At least the bottom wall is opaque to block out light under it when it is placed adjacent the earth. There are a plurality of openings substantially uniformly distributed through the bottom wall for the escape of water from the bladder to the earth underlying the bottom wall. A water entrance conduit extends from the interior of the bladder to the exterior thereof and functions as a conduit for supplying water to the bladder.

Most preferably, the size and distribution of the openings through the bottom wall are such that at least about two gallons of water will pass through the openings of a square meter of the bottom wall per minute when the water is incoming to the bladder at a rate sufficient to maintain the bladder in fully filled condition as water escapes through the pattern of openings of the bottom wall.

In conducting the method of the invention, the bladder is laid on the ground with its bottom porous wall adjacent the surface of the ground, and water is introduced into the bladder for passage through the bottom porous wall to saturate the earth underlying that porous wall. The bladder is sufficiently opaque to create a nighttime condition between it and the surface of the underlying earth. After a period of time, varying from about 5 minutes up to about 30 minutes, water saturation is terminated (or at a minimum is slowed) and an edge of the substantially flat and thin bladder is removed or lifted as by rolling it back from the surface of the ground, thereby exposing the saturated surface and revealing any earthworms, including night crawlers, that migrated out of the soaked earth to the surface of the earth. The earthworms, including night crawlers, seem to be relatively stunned by the treatment and do not seem to be as quick to move as when collected at nighttime. The simulated nighttime condition under the flat and thin bladder as well as the soaked earth condition fools the earthworms into believing their enjoyment of the surface of the earth is at nighttime, even though the activity for collection is conducted during the daytime. As the bladder is removed by lifting and folded or rolled away from the surface of the earth, the earthworms (which seem to be stunned) are relatively easily grabbed by hand and placed in a collection container. No washing or cleansing of the worms is necessary since no harsh chemicals are employed, and the person collecting the earthworms is not subjected to any unsafe condition.

Still other benefits and features and advantages of the invention will be evident as this description proceeds.

DESCRIPTION OF THE PREFERRED EMBODIMENT

Figure 1:
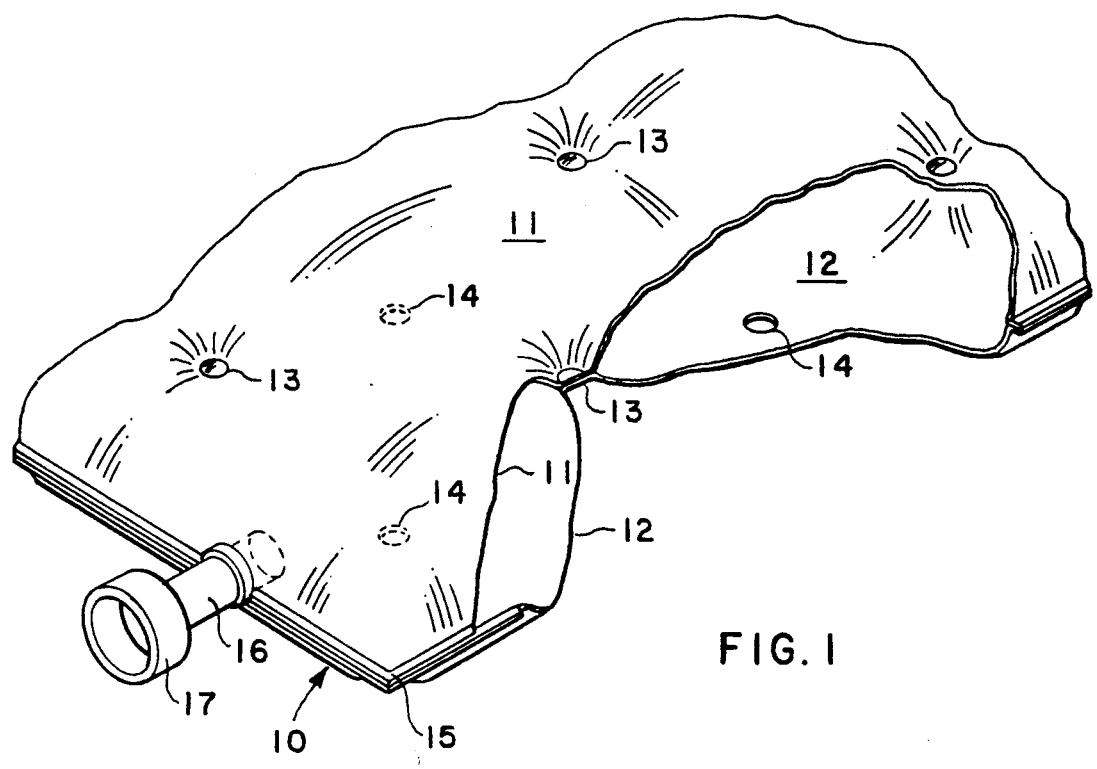
FIG. 1 is a perspective view of the bladder device of the invention, with parts broken away.
Figure 2:
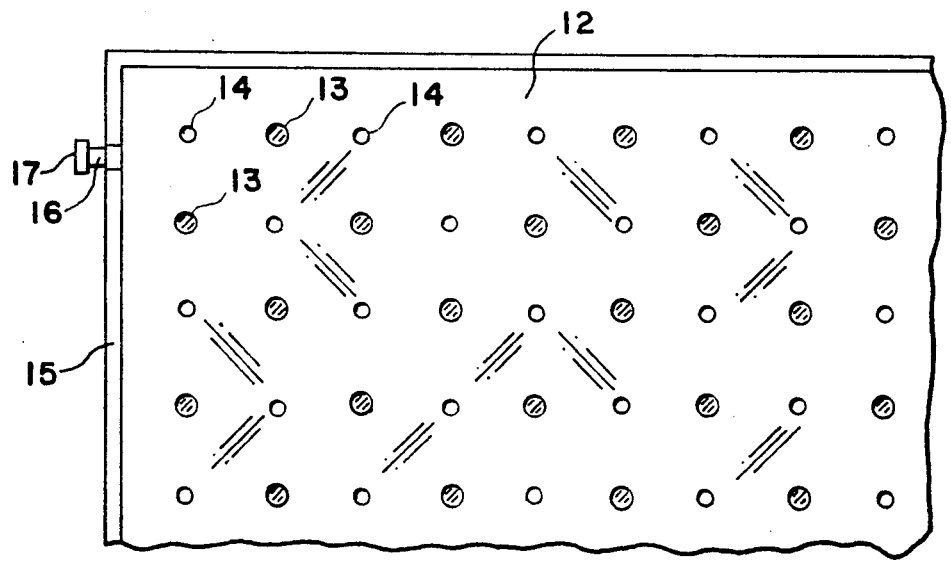
FIG. 2 is a plan view of the bottom wall or film of the bladder device, with parts broken away, and particularly illustrates a preferred pattern of apertures for creating the porosity of the bottom wall and a preferred pattern of spaced connections or joints between the top wall and bottom wall of the bladder.

Referring to the drawings, the new device comprises a flexible and substantially flat and thin bladder 10. The bladder is formed of walls that define the extent of its interior. The walls ideally comprise an upper or top wall 11 as well as a lower or bottom wall 12 formed of flexible sheet material. The flexibility of the sheet material forming the walls of the bladder is such that the bladder is easily laid in flat condition on the earth's surface. The maximum thickness between the top and bottom walls is not more than about 5 centimeters. This is true even when the bladder is fully filled with water. Area dimensions for the bladder, however, are much greater, for the reason that a significant area of the surface of the earth must be converted to a simulated nighttime condition as well as a drenching rain condition for the device of this invention to be effective. Thus, the bladder has an area dimension of at least about 1 meter (at least about one yard) in all dimensions transverse to its thickness but realistically should not have an area dimension greater than about 4 meters (about 4 or 5 yards) in all directions transverse to its thickness. Larger area dimensions tend to create more bulk than conveniently handled, and are unnecessary. One of the more ideal structures of the invention is one having an area dimension of about 4 feet (or a little more than 1 meter) by about 6 feet (or a little less than 2 meters).

The top 11 and bottom 12 walls of flexible sheet material defining the bladder are held against greater spacing from each other than about 5 centimeters by a plurality of spaced connections 13 therebetween. These connections may be formed in a variety of ways. For example, if desired, a pattern of spaced connections 13 may be formed by flexible but relatively inelastic pillars extending between and united to the top wall and bottom wall. More realistically, a pattern of spaced connections 13 may be formed by heat sealing or by adhesive sealing of the walls together at spots or points. When the top and bottom walls are formed of heat-sealable plastic films, as is most preferred, heat sealing at spots (e.g., spots relatively uniformly distributed), as illustrated in the drawing, is convenient. Alternately, if desired, adhesives may be employed such as, for example, a hot-melt adhesive from Black & Decker called "Thermogrip". Spot adhesive seals or connections between the top wall and bottom wall of flexible material are useful when the walls are formed of non-film materials such as woven materials.

The most ideal sheet material for forming the walls of the bladder is heat-sealable plastic film material of flexible nature. Illustrative such plastic film material may comprise polyethylene, polyvinyl chloride, polyurethane, or any of a variety of other plastic materials which form flexible (i.e., readily bendable and pliable and readily conformable to an underlying surface) films at thicknesses up to about 12 mils or about 300 microns. Thicker plastic films are unnecessary for practicing the invention, and indeed, are undesired since they add weight without adding benefits. The preferred range of thickness for useful film for making the bladder is between about 2 or 3 mils (about 50 or 75 microns) up to about 8 mils or 200 microns. Sometimes thickness above 8 mils or at about 10 mils (or 250 microns) may be desired, especially where the size of the bladder approaches area dimensions of 4 meters or so. Appropriate fillers and ingredients inhibiting degradation under exposure to weather and ultraviolet conditions are desirable for the protection of the plastic films. An important consideration is that of the opacity of the films The bladder itself should be such that, when placed upon the surface of the ground or earth, in flat condition, light is blocked out, so that the area occupied by the bladder on the surface of the ground or earth appears, from the earth side, to be a simulated nighttime condition or environment of darkness. Most preferably, the bottom or lower wall 12 of flexible material forming the bladder should be opaque to such a degree that the nighttime simulated condition is easily achieved upon laying the bladder in relatively flat condition upon the surface of grassy ground. It is convenient to employ opaque, dark plastic films (e.g., 8 mil polyethylene) using any appropriate dark pigments for both the top and the bottom flexible walls of the bladder.

The most convenient and economical formation of the bladder is accomplished by employing heat-sealable flexible plastic for both its top wall 11 and bottom wall 12 and by uniting the same at a perimeter edge 15 by heat sealing, as illustrated in the drawing. Useful bladders, however, may be fabricated employing a perimeter wall of about 2 or 3 centimeters in height to which both the upper 11 and bottom 12 main walls are secured or sealed. Further, if desired, a sheet material may be folded to form both the upper and lower walls of the bladder and thereby effectively form at least one edge as a continuum of material from the lower to the upper wall. The most preferred structures, however, are formed by heat sealing the entire perimeter of the upper and lower walls. This is because the lower wall must have a high porosity, and porosity of the upper wall is undesired. In fact, the upper wall 11 should be substantially impervious to the passage of water, even though that feature is not absolutely critical for the upper wall. The primary function of the upper wall is that of a closure or limiting wall. The difference in functions for the top or upper wall and bottom or lower wall make it preferable to employ separate sheet stock for each and to heat seal the entire perimeter.

The pattern of spacing for the connections 13 between the upper and lower wall must not interfere with relatively rapid movement of water from the water entrance or inlet to all portions and throughout the interior of the bladder. Thus, lines of connection, or lines of heat seal between the upper and lower walls are not preferred. They interfere with the rapid movement of water throughout all portions of the flat and thin bladder. The ideal connections between the upper and lower walls are what might be called spot connections in a spaced pattern effective to hold the maximum spacing of the upper or top wall 11 from the bottom wall 12 at no more than about 5 centimeters, and ideally, at no more than about 2 or possibly 3 centimeters. The reason for this is so as to minimize the weight of water per unit of area for the water-filled bladder on the surface of the earth. As compared to the bladder, it is the water that causes the dominant weight. Water weights usually should average not more than about 15 grams (about one-half ounce) per square inch of bottom wall surface, and never exceed more than about 0.04 pounds per square inch of bottom wall surface or never exceed more than about 20 grams per square inch. On a metric area basis, water weights on an average basis should never exceed about 4 grams per square centimeter, and preferably, on an average basis, should not exceed about 2 grams per square centimeter. These figures are to be considered as orders of magnitude and not absolutes. From a practical standpoint, the thickness of water within the bladder should not, under most conditions, exceed about one inch in height and preferably not exceed about a half inch in height for most ideal performance. In this manner, minimal water weight is added to the bladder on the surface of the ground, and the migration of earthworms out of the earth onto the surface beneath the bottom wall of the bladder is not significantly interfered with by any pressures from above on them. Thus it is that bladder thicknesses having a maximum of about 2 or 3 centimeters are rather ideal to employ since they preclude, or substantially preclude, the accumulation of sufficient water per unit of area to increase the weight of the bladder and water as a combination to the point of creating significant interference with migration of earthworms out of the earth onto the surface of the earth underneath the bottom wall.

Interestingly, even though the maximum thickness between the top and bottom walls should be kept relatively low as discussed, it is surprisingly possible to maintain the thickness within the limited thin range desired even when the anchor points or spots or connections 13 between the top and bottom walls are relatively distantly spaced, as for example, at distances two, four, or even up to possibly six or eight times the maximum thickness for a substantially flat and thin bladder. Thus, useful bladders satisfying the requirements of the invention may have a spacing between anchor fastening points 13 at approximately 20 centimeters even when the walls exhibit no greater spacing distance in use than about 4 centimeters. It should be recognized, however, that bladders of widely separated fastening points perform in this noted manner only when the porosity or perforations through the bottom wall are such as to allow water escape or passage at a rate about equal to the rate of incoming water through the incoming conduit 16 (without increasing the pressure of water in the bladder beyond a nominal increase generated by maintaining the bladder in fully filled condition).

The size and substantially uniform distribution of the holes or openings 14 through the bottom wall are such that saturation of the earth under the bottom wall is easily accomplished within a time range of approximately 5 minutes up to about 30 minutes, depending somewhat on the degree of moisture previously in the earth as a result of normal weather conditions. At a minimum, the size and substantially uniform distribution of the openings in the bottom wall are such as to pass about two gallons of water per square meter of the bottom wall per minute when the water supplied to the entrance conduit 16 is incoming at a rate sufficient to maintain the bladder in fully filled condition (as aforenoted) as the water continually passes through the bottom wall onto the ground or surface of the earth for soaking it. Highly porous fabrics can satisfy this criteria, but the preferred films of plastic should be punctured with apertures in order to effectively perform as required. A plurality of apertures or openings substantially uniformly distributed through the bottom wall may be provided in a variety of patterns. The size of useful holes or openings can vary from a fraction of a millimeter up to about a half centimeter, with the number of holes decreasing as size increases. Illustratively, a bladder of the invention having area dimensions of approximately 4 feet by 6 feet was equipped with about 80⅛ inch (slightly over 3 millimeter) diameter holes or apertures through its bottom film in a uniformly distributed pattern, with spots or points of anchoring between the top and bottom films spaced at intermediate locations between the 80 apertures. Incoming conduit 16 was fixed to a garden hose by connector 17. The water introduced was estimated to be at approximately 30 pounds per square inch of pressure at the hose connection. (Some household water tests up to approximately 60 pounds per square inch pressure, which is about the maximum normal water pressure one is apt to encounter for residential applications.) The exit of water through the apertures of the bottom wall was at the rate of about 5 gallons per minute per 24 square feet (i.e., per the size of the 4 by 6 foot bladder). This speed through the bottom wall was accomplished under bladder water pressure conditions which were nominally higher than mere water-drainage pressures (i.e., nominally higher than mere standing water pressures). A test on a grassy lawn in the afternoon following a rain which stopped at about 10 a.m. effectively caused the grassy area to be saturated or soaked within about 5 minutes, following which the water supply to the bladder was terminated and the bladder gently rolled back, revealing several earthworms as desired—all ready for collection. Either the worms seem to be stunned into cooperation or the daytime activity of collection contributes per se to the accuracy of hand movements in grabbing the worms. In any event, experience suggests that fewer problems of worm escape are encountered when using the technique of the invention.

Soaking the earth beyond about 30 minutes in practicing the invention is unnecessary. Generally a treatment period of soaking no greater than about 15 minutes is adequate. Worms desire more oxygen than present in soaked earth and thus voluntarily migrate to the earth's surface under the simulated nighttime conditions.

While practice of the invention may be accomplished on any earth surface reasonably expected to have earthworms burrowing under it, the preferred earth surface is not barren and has a grass cover. (Grass tends to cushion the weight of the water-filled bladder.) It is believed that this grass cushioning effect assists in providing a space above the surface of the earth and below the bottom wall of the bladder for the earthworms to occupy without suffering any significant pressure effects upon them.

The most ideal areas of grassy earth on which to practice the invention are those where the grass is relatively short and not sufficiently thick to afford a multiplicity of hiding places for the earthworms as they migrate to the earth's surface.

The spot connections between the bottom and top walls tend to cause, on filling the bladder with water, a modest "pillowing" effect which, to a degree, tends to lift portions of the bottom wall from the underlying earth and thus provide a haven of space for earthworms.

Those knowledgeable in this art will readily appreciate that this invention may be embodied in still other specific forms than illustrated without departing from the spirit or central characteristics of it. The illustrated embodiment is therefore to be considered illustrative and not restrictive, the scope of the invention being indicated by the appended claims rather than the foregoing description; and all variations that come within the meaning and range of equivalency of the claims are intended to be embraced thereby.

That which is claimed is:

1. A device for causing earthworms to migrate to the earth's surface for easy collection, said device comprising a flexible, substantially flat and thin bladder capable of being laid in flat condition on the earth's surface and having a top wall and a bottom wall of flexible sheet material defining the top and bottom limits of the bladder interior, said bladder having a maximum interior thickness between said top wall and bottom wall of not over about 5 centimeters when said bladder is filled with water after being laid in flat condition on the surface of the earth, said bladder having area dimensions greater than about 1 meter in all directions transverse to said thickness and not greater than about 4 meters in all directions transverse to said thickness, said maximum thickness of said bladder being limited by the fact that said top wall and said bottom wall are held against greater spacing from each other than about 5 centimeters by a pattern of spaced connections therebetween, at least said bottom wall being opaque to block out light under it when it is placed adjacent the earth, there being a plurality of openings substantially uniformly distributed through said bottom wall for the escape of water from said bladder to earth underlying said bottom wall, and a water entrance conduit extending from the interior of said bladder to the exterior thereof and functioning as a conduit for supplying water to said bladder.

2. The device of claim 1 wherein the size and substantially uniform distribution of said openings through said bottom wall are such that at least about two gallons of water will pass through the openings of a square meter of the bottom wall per minute when the water supplied through said water entrance conduit is incoming at a rate sufficient to maintain the bladder in fully filled condition as water continually escapes through the openings of the bottom wall.

3. The device of claim 1 wherein said maximum thickness between said top wall and bottom wall is limited to no more than about 2 centimeters by said spaced connections therebetween.

4. The device of claim 1 wherein said openings of said bottom layer have a size greater than about 3 millimeters in diameter and are in a pattern such that the greatest spacing between adjacent openings is not in excess of 20 centimeters.

5. The device of claim 1 wherein said top and bottom walls are formed of plastic film and said openings are apertures in the plastic film of said bottom wall.

6. A method for collecting earthworms comprising:
   a) laying a substantially flat and thin bladder on an area of the earth's surface where the underlying earth contains a random distribution of earthworms, said bladder being sufficiently opaque to block out light penetration through it to the underlying earth, and said bladder having a bottom wall adjacent the earth's surface equipped with openings for the passage of water therethrough to soak the earth therebeneath,
   b) continuously supplying water to said bladder for passage through the openings of the bottom wall of said bladder into the earth underlying said bottom wall so as to soak the earth underlying said bottom wall within a period of time from about 5 minutes up to about 30 minutes, to thereby stimulate earthworms in the underlying earth to migrate out of the soaked earth onto the area of the earth's surface underneath said bottom layer,
   c) sequentially removing limited portions of said bladder from the earth's surface while simultaneously, as each portion of the earth's surface is exposed, collecting earthworms that have migrated to the earth's surface and lie thereupon at the time the portion of the bladder is removed therefrom, and
   d) placing collected earthworms in a container as they are collected.

7. The method of claim 6 wherein said laying step is preceded by the step of providing said bladder with bottom wall openings of a size and substantially uniform distribution as to pass at least about two gallons of water per minute through a square meter of said bottom wall when said step of continuously supplying water to said bladder is conducted.

8. The method of claim 6 wherein said water is supplied to said bladder at a rate about equal to the rate at which water passes through said openings of said bottom wall.

9. The method of claim 6 conducted so as to maintain the height of water within said bladder below about 3 centimeters so as to minimize the weight of bladder water per unit of area of the underlying earth.

* * * * *